(12) United States Patent
Nollert

(10) Patent No.: US 12,064,135 B2
(45) Date of Patent: Aug. 20, 2024

(54) CATHETER WITH RADIALLY EXPANDABLE SCORING ELEMENT

(71) Applicant: BIOTRONIK AG, Buelach (CH)

(72) Inventor: Georg Nollert, Strasslach (DE)

(73) Assignee: BIOTRONIK AG, Buelach (CH)

( * ) Notice: Subject to any disclaimer, the term of this patent is extended or adjusted under 35 U.S.C. 154(b) by 677 days.

(21) Appl. No.: 17/097,282

(22) Filed: Nov. 13, 2020

(65) Prior Publication Data

US 2021/0177454 A1 Jun. 17, 2021

(30) Foreign Application Priority Data

Dec. 11, 2019 (EP) .................................. 19215220

(51) Int. Cl.
| | | |
|---|---|---|
| *A61B 17/3207* | (2006.01) | |
| *A61M 25/10* | (2013.01) | |
| *A61M 29/00* | (2006.01) | |
| A61B 17/00 | (2006.01) | |
| A61M 25/00 | (2006.01) | |

(52) U.S. Cl.
CPC ... *A61B 17/320725* (2013.01); *A61M 25/104* (2013.01); *A61M 29/00* (2013.01); *A61B 2017/00853* (2013.01); *A61B 2017/00867* (2013.01); *A61M 25/0074* (2013.01); *A61M 2025/1043* (2013.01); *A61M 2025/1086* (2013.01)

(58) Field of Classification Search
CPC .. A61B 17/320725; A61B 2017/00853; A61B 2017/00867; A61B 17/3207; A61B 2017/320741; A61M 29/00; A61M 25/0074; A61M 2025/0079; A61M 2025/0096; A61M 25/0021; A61M 2025/0024; A61M 25/104; A61M 2025/0025; A61M 25/0023
See application file for complete search history.

(56) References Cited

U.S. PATENT DOCUMENTS

| | | | |
|---|---|---|---|
| 5,279,565 A | 1/1994 | Klein et al. | |
| 2014/0277073 A1* | 9/2014 | Calderon | A61B 17/3417 606/198 |
| 2015/0246211 A1* | 9/2015 | Bunch | A61M 25/0074 128/200.26 |
| 2018/0056051 A1* | 3/2018 | Kabra | A61M 25/0102 |

FOREIGN PATENT DOCUMENTS

WO 2015195606 A1 12/2015

OTHER PUBLICATIONS

European Search Report from the corresponding European Patent Application No. 19215220, dated Jun. 19, 2020.

* cited by examiner

*Primary Examiner* — Majid Jamialahmadi

(74) *Attorney, Agent, or Firm* — Greer, Burns & Crain, Ltd.; Steven P. Fallon

(57) ABSTRACT

A catheter for dilating and/or destroying a stenosis in a vessel of a patient includes a catheter shaft having a cavity, at least one first active element within the cavity fixedly connected to a wall delimiting the cavity, and at least one radially protruding scoring element arranged on the outside of the catheter shaft at the cavity for exerting a pressure force on a stenosis in a vessel. The at least one first active element is configured to react to an axially movable element by radially expanding the catheter shaft and thereby radially expanding the at least one radially protruding scoring element.

11 Claims, 2 Drawing Sheets

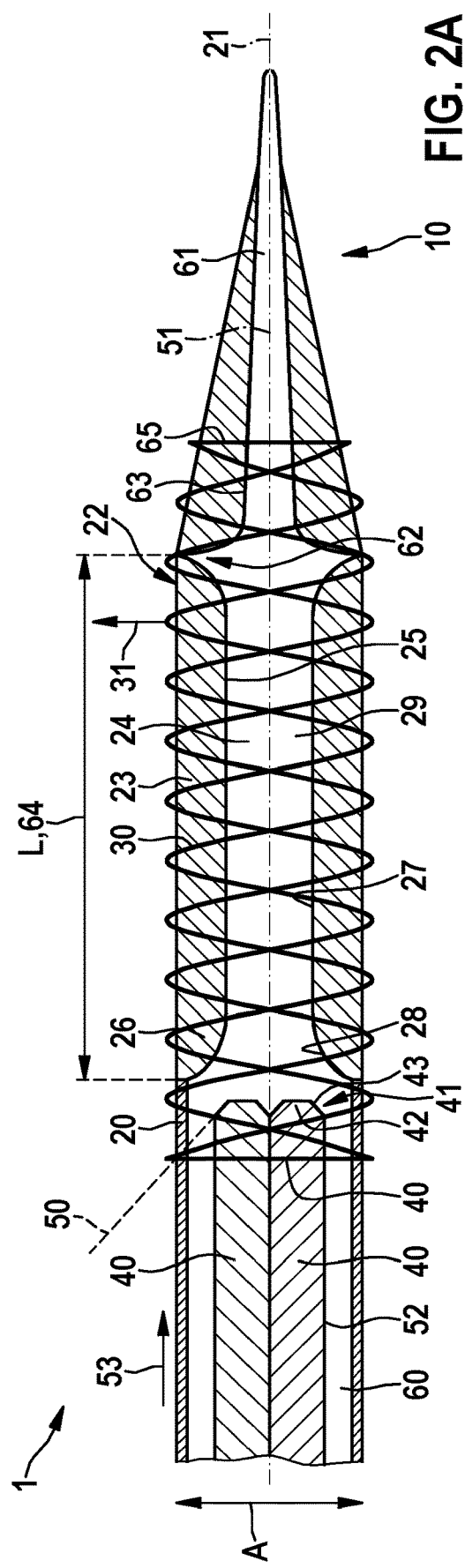
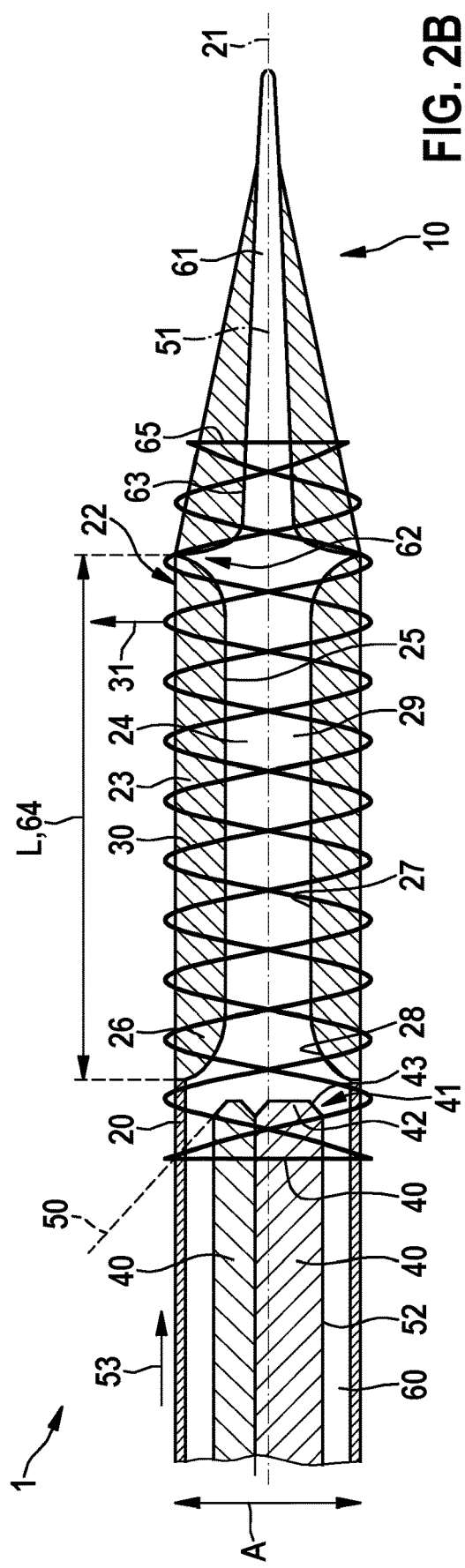
FIG. 2A
FIG. 2B

CATHETER WITH RADIALLY EXPANDABLE SCORING ELEMENT

PRIORITY CLAIM

This application claims priority under 35 U.S.C. § 119 and all applicable statutes and treaties from prior European Application EP 19215220, filed Dec. 11, 2019.

FIELD OF THE INVENTION

A field of the invention is catheter devices for treatment of fibrotic and calcific stenoses.

BACKGROUND

Balloon catheters, in the form of what are known as scoring or cutting balloons, are frequently used for pre-dilation, for dissecting fibrotic and calcific stenoses. Such a scoring balloon catheter includes a balloon, having at least one elongated contact element fixed onto the surface thereof facing the outside, the contact element also being referred to as a scoring element.

In addition, scoring elements that are formed by a wire mesh or by individual elements adhesively bonded to the balloon surface are known. These balloons cut or score the intima and media of the artery, thereby breaking up calcifications or cutting through scarring (fibrosing) of the vascular constrictions.

Scoring balloons including circumferential blades have been found to cause fewer injuries than cutting balloons including straight blades. These balloons have a defined diameter and length, so that many of these balloons have to be kept in stock to be able to treat different stenoses.

When the balloons used nestle against a vasoconstriction, it is furthermore possible for tightening or radial narrowing of the balloons to occur, due to a lower hardness of the outside of the balloons compared to the stenosis. This results in an increase in the bearing surface of the balloon against the stenosis, and thus in a reduction of the pressure that is applied to the stenosis, thus running counter to the intended treatment effect.

In addition, this means that the balloon yields in severely hardened areas, and that the hard portion of the vasoconstriction is not dilated to the same extent as the remainder of the vasoconstriction.

SUMMARY OF THE INVENTION

A catheter for dilating and/or destroying a stenosis in a vessel of a patient includes a catheter shaft having a cavity, at least one first active element within the cavity fixedly connected to a wall delimiting the cavity, and at least one radially protruding scoring element arranged on the outside of the catheter shaft at the cavity for exerting a pressure force on a stenosis in a vessel. The at least one first active element is configured to react to an axially movable element by radially expanding the catheter shaft and thereby radially expanding the at least one radially protruding scoring element. A system includes a plurality of advancement elements having a plurality of radial widths as the axially movable element. Selecting of the suitable advancement element permits stenoses in various diameter ranges, and also various lengths to be optimally and reliably treated, with a single catheter shaft of the invention.

BRIEF DESCRIPTION OF THE DRAWINGS

Further features and advantages of the invention will be described in the description of an exemplary embodiment of the invention, based on the figure. In the drawing:

FIGS. 2A-2B show sectional views of a catheter according to FIG. 1 with a plurality of advancement elements having a plurality of radial widths.

DETAILED DESCRIPTION OF THE PREFERRED EMBODIMENTS

Figure 1:
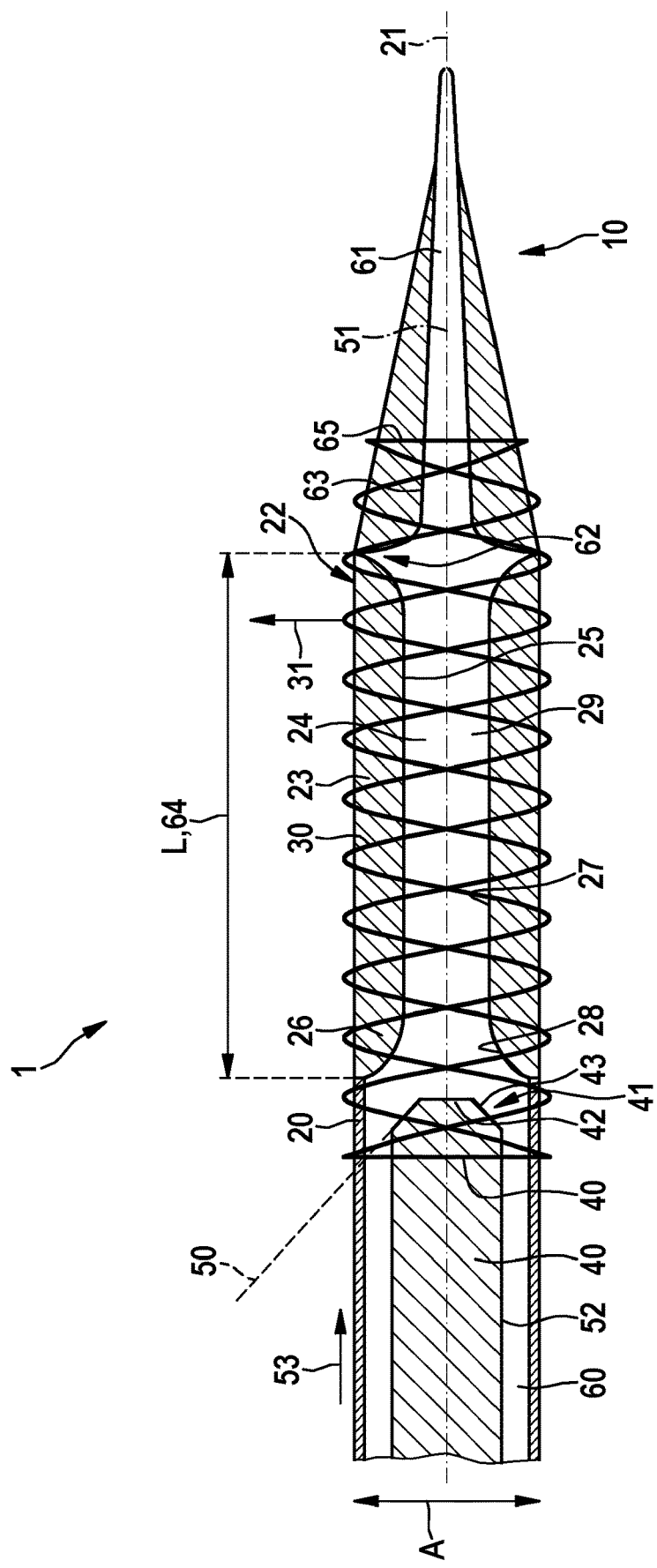
FIG. 1 shows a sectional view of an embodiment of a catheter according to the invention.

In the following description, the terms "radial" and "axial" refer to the longitudinal axis of the catheter shaft. The cavity, which is also referred to as lumen, is essentially formed at a distal end portion of the catheter, inside the catheter shaft, coaxially with respect to the outside. In particular, the cavity can be designed to be axially open on one side.

When a body carries out a movement on the inclined plane, this body increases the distance thereof with respect to the base of the inclined plane. This increase in distance is utilized according to the invention for radially expanding the catheter shaft. In this way, the scoring element protruding radially outwardly from the outside of the catheter shaft can be pushed against a stenosis or lesion, dilating or destroying it.

The catheter according to the invention accordingly has the advantage that a radial expansion of the shaft can be achieved by a simple, in particular manual, actuation of the principle of action of the inclined plane, and a force can be applied accordingly efficiently, and with fine precision, in the radial direction on a wall of a vessel, or stenosis present there, so as to mechanically dilate or destroy the stenosis.

The catheter according to the invention is accordingly configured as a scoring catheter for so-called scoring, for the purpose of dilating a vessel.

The first active element can be, in particular fixedly, arranged at the wall delimiting the cavity, or be an integral part of this wall.

Instead of a balloon including blades, the invention is based on an expandable so-called sheath including blades as scoring elements. By inserting advancement elements having various diameters, also referred to as dilators, forward, the sheath can assume various diameters. Depending on the depth to which the dilator is inserted, the length of the radially expanding length range is also variable.

According to one embodiment of the invention, it is provided that the catheter furthermore includes an advancement element to be inserted and/or moved into the cavity along the longitudinal axis of the catheter shaft, wherein the advancement element includes a second active element for creating the principle of action of the inclined plane, which bears against, or can bear against, the first active element so that, during a relative movement between the two active elements, a wedge action can be implemented, by which a radial expansion of the catheter shaft can be generated.

For this purpose, the catheter, adjoining the cavity, forms a channel through which the advancement element leads to a proximal end region of the catheter, for the purpose of manually actuating the advancement element at the proximal end. The second active element bears against the first active element after an advancement movement of the advancement element has been carried out.

The advancement element, at the proximal end region thereof, can include at least one marking, in particular multiple markings provided along the longitudinal extension direction of the advancement element, based on which a person operating the catheter according to the invention obtains information with respect to the insertion depth of the advancement element into the catheter shaft, and thus with respect to the length of the radial expansion. The catheter according to the invention has the advantage that, with sufficient elasticity of the wall delimiting the cavity, or of the material of the catheter shaft, advancement elements of various radial widths or various diameters can be pushed into the cavity, which correspondingly effectuate various radial expansions, or, by way of the wedge action, implement various radial forces, as a function of the radial deformability of the outside of the catheter shaft.

In one embodiment, it is provided that one of the two active elements includes a bearing surface, and the respective other active element includes an inclined surface, so that the first active element is moved radially outwardly when the inclined surface bears against the bearing surface, and when an advancement movement of the advancement element is carried out.

This radially outward movement is implemented by the principle of the inclined plane, or by the wedge action, against a possibly present elastic restoring force of the catheter shaft. In the process, an inclination is defined in relation to the longitudinal axis of the catheter shaft.

In particular, it may be provided that the first active element has a bearing surface at the catheter shaft, and the second active element of the advancement element has an inclined surface. However, the invention also does not preclude a reverse configuration of the active elements. Moreover, the bearing surface itself may also be inclined or likewise form an inclined plane, which amplifies the wedge action.

An advantageous embodiment provides that a respective step adjoins the particular surface in the axial direction so that, after a wedge action-induced expansion of the catheter shaft and during a further advancement movement, the steps can be made to bear radially against one another.

The particular step extends as far radially as the radially furthest point of the particular surface. This means that the step adjoining the bearing surface extends as far radially inward as the maximum radial extension of the bearing surface itself, when this bearing surface is arranged or formed at the first active element, and thus at the catheter shaft.

The step adjoining the inclined surface extends as far radially outward as the maximum radial extension of the inclined surface itself when the inclined surface is arranged or formed at the second active element, and thus at the advancement element.

The length of the insertion region of the steps determines the length of the radial enlargement or expansion of the catheter shaft, and thus the length across which, according to the invention, a pressure force is applied to the vessel wall.

It is furthermore ensured by steps that, at least across the length of the steps, no radial constriction of the outside of the catheter shaft can occur, as it may occur with balloon catheters.

Moreover, a lumen that extends into the distal end region of the catheter can adjoin the cavity provided for the radial expansion, the lumen being used to receive a guide element, such as a guide wire, for the purpose of inserting the catheter into a vessel of a patient.

At least one radially inwardly protruding shoulder can be arranged in the transition region between the cavity and this lumen, so as to implement a mechanical blocking action of an advancement movement of the advancement element. The distal end of the catheter according to the invention is preferably designed to be pointed or conical so as to facilitate the insertion into a vessel.

The first active element as well as the second active element, in a plane perpendicular to the longitudinal axis, are advantageously formed completely around this longitudinal axis.

In particular, it is provided that both the first active element and the second active element are designed to be rotation-symmetrical with respect to the longitudinal axis, surrounding the same. In this way, in particular the first active element can have the shape of a hollow frustum, and the second active element can, at least in sections, have the shape of a cone, which during a movement of the hollow frustum radially expands the same, and in this way overall achieves a radial expansion of the catheter shaft. Accordingly, in this embodiment, the inclined surface is the lateral surface of a cone or frustum, and the bearing surface is the lateral surface of a hollow frustum.

In the process, an embodiment in which at least one of the two active elements is only implemented as segments that are spaced apart on a circumferential path about the longitudinal axis so as to facilitate a radial expansion of the catheter shaft shall also not be precluded by the invention.

For the purpose of facilitating an expansion, the inclined surface and/or the bearing surface can have a curved progression in a plane in which the longitudinal axis is located. This means that a particular surface implementing the wedge principle can have a concavely or convexly curved design. In particular, the bearing surface of the first active element can have a convex curvature, which makes it easier for a conical second scoring element to be pushed, while self-centering, into the first active element, and thereby expand the first active element, and thus the catheter shaft.

In an advantageous embodiment, it is provided that the catheter shaft has an outside wall that is closed on the circumference and delimits the cavity, wherein the outside wall is radially expandable. This configuration is in particular implemented in the longitudinal section of the catheter shaft in which the radially expandable cavity is positioned. This is in particular made possible through the use of an elastically expandable material for the outside wall.

The advancement element can be a bendable rod, in particular a push rod, for axially displacing the second active element.

For manually actuating the advancement element, it is in particular provided that this push rod protrudes from the catheter shaft at the proximal end.

The scoring element can have an elongated configuration that, along the longitudinal extension thereof, surrounds the circumference of the catheter shaft.

In the process, the scoring element can be helically arranged on the outside of the catheter shaft.

This embodiment has the advantage that, when a rotational movement of the catheter shaft is carried out, not only a radial component of an exerted pressure force, but also an axial component can be exerted on a stenosis, so that the stenosis is subjected to a multi-axial load, and thereby can be removed more efficiently and/or thoroughly.

In particular, the scoring element can be arranged in the form of a double helix or triple helix on the outside of the catheter shaft.

The scoring element can have a lesser width at the radially outer region thereof than in the region of the mechanical fixation thereof to the outside of the catheter shaft. This has the advantage that a concentrated, high pressure force is exerted on a stenosis for the purpose of dilating and/or splitting or breaking it up.

In one embodiment of the catheter, it is provided that the scoring element, distally adjoining the helical shape, includes a ring, which is fixed in the axial direction/in the circumferential direction to the outside of the catheter shaft. Such a ring can help prevent the advancement element from being pushed through the catheter beyond the end.

The material of the ring is preferably a nickel-titanium alloy, which allows a relatively large radial expansion, and thus enables a certain flexibility. In particular, a shape memory alloy can be used as the material of the ring, such as nitinol.

The ring, however, does not necessarily have to be axially fixed at the scoring element, but it suffices when the ring as well as the scoring element are positioned in such a way that, during an axial relative movement between these components, a pressure force can be transmitted between these.

In particular, such a ring is arranged so as to secure the position of the scoring element in the axial direction, in particular when it has a helical design. Such a ring is advantageously arranged outside the axial longitudinal section of the catheter shaft, which undergoes the radial expansion during the insertion of the advancement element.

The material of the catheter shaft is preferably made of suitable polymers, also in the form of a composite including more than one polymer, or a composite including one or more polymers and a metal component. Examples of suitable polymers are polypropylene, polyethylene, polyethylene terephthalate, polyamide, polyimide, polyamide copolymers, polyether block amide, silicone or silicone-based materials. The material of the scoring element is made of nitinol, stainless steel, or polycarbonate, for example.

The materials used ensure reliable radial force transmission for the purpose of exerting pressure on a stenosis, while providing relatively low flexural rigidity for adapting the catheter or catheter shaft to the winding arteries of the vascular system.

An outer casing, also referred to as an outer sheath, can be another component of the catheter according to the invention, which can be pushed into the vessel to be treated by a guide element, such as a guide wire. This guide element is then likewise used to guide and position the actual catheter shaft.

Furthermore, a catheter system is disclosed, including at least one catheter according to the invention as well as multiple advancement elements of various radial widths.

This means that the catheter system includes at least one catheter shaft configured in accordance with the invention, and a set of different advancement elements, the respective second active elements of which have differently large radial extensions so as to achieve differently large radial expansions, in cooperation with the catheter shaft or the first active element located there.

The advantage of this catheter system according to the invention is in particular that, when only one catheter shaft is kept available and the suitable advancement element is selected, stenoses in various diameter ranges, and also various lengths, can be optimally and reliably treated, without having to replace the catheter shaft.

One advantage of the catheter or catheter system according to the invention is in particular that the number of required devices is reduced, since only one catheter shaft has to be kept available, and different advancement elements, having a simple design and various radial sizes, can be used to be able to optimally treat stenoses of various inside diameters or of various lengths. By way of such a system, it is furthermore possible to incrementally carry out a dilation or treatment of stenoses by sequentially utilizing the various advancement elements or dilators, in accordance with the increase in the radial width thereof, in the same catheter shaft.

Furthermore, inadvertent radial constrictions, as they frequently occur with balloons, are not to be expected with the catheter according to the invention since the outside thereof can be made of a considerably harder or firmer material than an expanded balloon, and moreover the fixed mechanical connection, due to the principle of the inclined plane inside the catheter shaft, ensures defined mechanical bracing, so that no inadvertent radial narrowing of the catheter can occur.

FIG. 1 shows an embodiment of a catheter 1 according to the invention, which is used to dilate a stenosis in a patient's vessel. For this purpose, the catheter 1 includes a flexible catheter shaft 20 that extends along a longitudinal axis 21 and extends from a proximal end portion, which is not shown here, to a distal end portion 10. On the outside 22 of an outside wall 23, which has a substantially cylindrical design, the catheter shaft 20 includes a scoring element 30 designed, by way of example, in the form of a double helix.

This scoring element 30 can be fixedly connected to the outside wall 23. The scoring element 30 protrudes radially from the outside wall 23. At the two axial end regions, it bears against a respective ring 65, which itself, however, does not have to be fixed in the circumferential direction.

In the process, the scoring element 30 extends, in the longitudinal direction of the catheter shaft 20, beyond a region in which the outside wall 23 of the catheter shaft 20 forms a first step 29 delimiting an inner cavity 24. This first step 29 thus delimits, with an inner wall 25, the cavity 24.

At an end region facing away from the distal end portion 10, the first step 29 includes a first active element 26, which includes a bearing surface 27 having a convex curvature 28. An advancement element 40 in the form of a push rod is arranged movably along the direction of the longitudinal axis 21, in a channel 60 in the catheter shaft 20. At the end region facing the distal end portion 10, the advancement element 40 includes a second active element 41, which in the form of a frustum 42, defines an inclined surface 43, which can be made to bear against the first active element 26 or the bearing surface 27 thereof. The first active element and the second active element together then form the principle of action of the inclined plane 50, which makes it possible, during an advancement movement 53 along the longitudinal axis 21, to implement the increase in a distance A with respect to the base 51 of the inclined plane 50 with little force expenditure.

Correspondingly, during a further advancement movement 53 of the scoring element 30, the frustum 42 of the advancement element 40 enters the first active element 26, which is essentially designed as a hollow cone, and thereby radially expands the first active element 26. Due to the fixed connection between the first active element 26 and the outside wall 23 of the catheter shaft 20, the overall distance A is increased, thus resulting in a radial expansion of the catheter shaft 20.

A pressure force 31 can be accordingly exerted in the radial direction from the outside 22 of the catheter shaft 20, and by the scoring element 30 arranged there, on a stenosis or vascular wall surrounding the catheter shaft 20.

If the advancement element 40 was displaced so much that the two active elements 26, 41 were moved past one another, the first step 29 of the catheter shaft 20 and the second step 52 of the advancement element 40 bear against one another in the radial direction.

This results in very high compressive strength of the catheter 1 in the overlapping region. Depending on how deep the advancement element 40 is pushed into the catheter shaft 20, it is possible to determine the length of the axial longitudinal section of the radial expansion 64. It is apparent that the length of the axial longitudinal section of the radial expansion 64 cannot be greater than the length L of the first step, since a shoulder 63 adjoins in an overlapping region 62 between the end region of the first step 29 facing the distal end portion 10 and a wall delimiting a distally terminal lumen 61, the shoulder extending further radially inward than the first step 29, so that the advancement element 40 is stopped in the advancement movement 53 thereof by this shoulder 63.

This suppresses an inadvertent expansion of the catheter shaft 20 outside the longitudinal section that is provided with the scoring element 30.

A guide wire (not shown here), which can extend through the catheter shaft 20, for positioning the same, into the distally terminal lumen 61, however, is not impeded by this.

Using the catheter 1 according to the invention or the catheter system according to the invention, it is thus possible in a simple as well as a reliable and cost-effective manner to pretreat, or treat, or eliminate stenoses or deposits in vessels of patients by way of dilation and/or destruction. If differently thick advancement elements 40 are used, accordingly differently wide radial expansions can be implemented. Due to the high compressive strength of the catheter shaft 20 as well as of the scoring element 30, no radial constrictions or deformations are to be expected. The length of the radial expansion can be influenced by the insertion length of the advancement element 40 or dilator, and accordingly also the length of the sections of the vessel itself to be treated.

FIGS. 2A-2B show a catheter 1 having a plurality of advancement elements 40 as the axial movable element. The plurality of advancement elements 40 have a plurality of radial widths

The invention claimed is:

1. A catheter for dilating and/or destroying a stenosis in a vessel of a patient, comprising a catheter shaft having a cavity, at least one first active element within the cavity fixedly connected to a wall of the catheter shaft delimiting the cavity, and at least one radially protruding scoring element arranged on the an outside of the catheter shaft at the cavity for exerting a pressure force on a stenosis in a vessel, wherein the at least one first active element is configured to react to an axially movable element by radially expanding the catheter shaft and thereby radially expanding the at least one radially protruding scoring element, wherein the at least one first active element comprises a bearing surface with a convex curvature and wherein the axially movable element comprises an inclined surface configured to first engage the convex curvature during an advancement movement of the axially movable element within the cavity to radially expand the catheter shaft.

2. The catheter according to claim 1, wherein the at least one first active element and the axially movable element are formed completely around a longitudinal axis of the catheter shaft in a plane perpendicular to the longitudinal axis.

3. The catheter according to claim 1, wherein the axially movable element is a bendable push rod.

4. The catheter according to claim 1, wherein the at least one scoring element has an elongated configuration that surrounds a circumference of the catheter shaft along the a longitudinal extension thereof.

5. The catheter according to claim 4, wherein the at least one scoring element comprises a helical structure on the outside of the catheter shaft.

6. The catheter according to claim 5, wherein the helical structure comprises a double helix.

7. The catheter according to claim 5, wherein the at least one scoring element has a lesser width at a radially outer region thereof than in a region of mechanical fixation to the outside of the catheter shaft.

8. The catheter according to claim 7, wherein the at least one scoring element comprises a ring which is fixed in the region of mechanical fixation in an axial direction and in a circumferential direction on the outside of the catheter shaft.

9. The catheter according to claim 1, wherein the catheter shaft is formed of a material selected from polypropylene, polyethylene, polyethylene terephthalate, polyamide, polyimide, polyamide copolymers, polyether block amide, and silicone or silicone-based materials.

10. The catheter according to claim 1, wherein the at least one scoring element is formed of a material selected from nitinol, stainless steel or polycarbonate.

11. A catheter system, comprising the catheter according to claim 1, further comprising additional axially movable elements, wherein the additional axially movable elements comprise a plurality of radial widths.

* * * * *